(12) United States Patent
Domanik

(10) Patent No.: US 9,463,137 B2
(45) Date of Patent: Oct. 11, 2016

(54) METHODS, PACKAGING AND APPARATUS FOR COLLECTION OF BIOLOGICAL SAMPLES

(71) Applicant: CYTOCORE, INC., Chicago, IL (US)

(72) Inventor: Richard A. Domanik, Chicago, IL (US)

(73) Assignee: Cytocore Inc, Chicago, IL (US)

( * ) Notice: Subject to any disclaimer, the term of this patent is extended or adjusted under 35 U.S.C. 154(b) by 0 days.

(21) Appl. No.: 14/397,447

(22) PCT Filed: Mar. 15, 2013

(86) PCT No.: PCT/US2013/032042
§ 371 (c)(1),
(2) Date: Oct. 27, 2014

(87) PCT Pub. No.: WO2013/162756
PCT Pub. Date: Oct. 31, 2013

(65) Prior Publication Data
US 2015/0122686 A1 May 7, 2015

Related U.S. Application Data

(60) Provisional application No. 61/639,910, filed on Apr. 28, 2012.

(51) Int. Cl.
*B65D 77/06* (2006.01)
*A61J 1/14* (2006.01)
*A61B 10/00* (2006.01)

(52) U.S. Cl.
CPC ............ *A61J 1/14* (2013.01); *A61B 10/0045* (2013.01); *A61B 10/0096* (2013.01); *B65D 77/06* (2013.01); *A61B 2010/0074* (2013.01)

(58) Field of Classification Search
CPC .......... A61B 10/0045; A61B 10/0096; A61B 2010/0074; A61J 1/14; B65D 77/06
USPC ......................................... 206/438, 569–572
See application file for complete search history.

(56) References Cited

U.S. PATENT DOCUMENTS

| 2,844,150 A | 7/1958 | Draghi |
| 2,973,131 A | 2/1961 | Mead et al. |
| 3,340,116 A | 9/1967 | Naito |
| 3,579,303 A * | 5/1971 | Pickering ................ B01L 3/505 206/438 |

(Continued)

FOREIGN PATENT DOCUMENTS

| CN | 1138448 A | 12/1996 |
| CN | 1468368 A | 1/2014 |

(Continued)

OTHER PUBLICATIONS

Search Report and Written Opinion issued in Int'l App. No. PCT/US2013/032042 (2013).

(Continued)

*Primary Examiner* — Bryon Gehman

(57) ABSTRACT

Methods, apparatus and compositions are disclosed for collection and transport of biological samples for testing and/or evaluation by a clinical laboratory. In particular, the disclosure relates to the self-collection of such samples by subjects providing the samples. Self-collection is necessary in some situations e.g. where a subject's religion prohibits being touched by a non-family member and subjects at great distance from medical facilities.

11 Claims, 10 Drawing Sheets

(56) References Cited

U.S. PATENT DOCUMENTS

| | | |
|---|---|---|
| 3,983,873 A | 10/1976 | Hirschman |
| 4,549,655 A * | 10/1985 | Forsythe, Jr. ........ G01N 33/525 206/569 |
| 4,561,543 A | 12/1985 | Thompson |
| 4,637,061 A * | 1/1987 | Riese .................... B65D 31/12 206/569 |
| 5,256,571 A | 10/1993 | Hurley et al. |
| 5,415,282 A | 5/1995 | Kienholz |
| 5,575,047 A | 11/1996 | Gerstenberger et al. |
| 5,916,205 A | 6/1999 | Olson et al. |
| 6,183,456 B1 | 2/2001 | Brown et al. |
| 6,423,550 B1 | 7/2002 | Jenkins et al. |
| 6,776,059 B2 | 8/2004 | Kunimune et al. |
| 7,510,080 B2 * | 3/2009 | Smart ..................... A45C 3/00 206/570 |
| 2002/0165673 A1 | 11/2002 | Morgan |
| 2008/0254471 A1 | 10/2008 | Bordano |

FOREIGN PATENT DOCUMENTS

| | | |
|---|---|---|
| JP | H08-320276 A | 12/1996 |
| WO | WO 99/31273 | 6/1999 |

OTHER PUBLICATIONS

Office Action issued in Chinese App. No. 201380034084.4 (Dec. 1, 2015).

* cited by examiner

METHODS, PACKAGING AND APPARATUS FOR COLLECTION OF BIOLOGICAL SAMPLES

CROSS REFERENCE TO RELATED APPLICATIONS

This application is a U.S. nationalization under 35 U.S.C. §371 of International Application No. PCT/US2013/032042, filed Mar. 15, 2013, which claims priority from U.S. Ser. No. 61/639,910 filed Apr. 28, 2012. The disclosures set forth in the referenced applications are incorporated herein by reference in their entireties.

BACKGROUND

Methods, apparatus and compositions are disclosed for collection and transport of biological samples for testing and/or evaluation by a clinical laboratory. In particular, the disclosure relates to the self-collection of such samples by subjects providing the samples.

Tests performed by a clinical laboratory are often classified as being "screening", "diagnostic" or "monitoring" depending upon the target population and the intended use of the test results. Screening tests are typically performed on large asymptomatic populations for the purpose of identifying the relatively few individuals within that population who have the target disease or a precursor condition thereto. Screening tests targeting risk factors for the development of a disease, rather than the disease itself, have recently been introduced and are beginning to be deployed. Early detection is a primary goal of screening programs. It has been well documented that not only does early detection of a disease and consequent early intervention generally improve the outcome for individual subjects, but it can significantly reduce the cost of healthcare on a system basis by reducing the number of subjects who progress to an advanced and more resource consuming stage of the disease. Diagnostic tests are typically performed on individual subjects who are known or strongly suspected to have a particular disease for the purposes of confirming or refuting the presence of the disease and, if present, classifying it in terms of stage and other characteristics to assist a physician in treatment planning and subject management. Monitoring tests are primarily used to track the progression of a disease or the effectiveness of a treatment in an individual subject over time.

Even if a given test can be used for screening, diagnosis and monitoring, the differences in target populations and intended uses impose significantly different requirements on these various embodiments. In many respects screening tests are the most challenging to develop and deploy as the diseases that are generally targeted in screening programs have relatively low incidence rates in the population to be screened. Therefore large to very large numbers of individuals must be tested in a relatively short period of time in order for a screening program to have any significant impact upon public health. Screening programs generally operate under stringent resource constraints, particularly with respect to funding and the availability of medically trained personnel and, in many cases, are conducted in geographic areas that have limited transportation and communications infrastructures. Operational efficiency, logistics and cost-per-result are therefore exceptionally important in screening programs.

Due in part to shortages of the medically trained personnel who are traditionally employed to collect samples in screening programs, there has been a growing demand for methods and devices that allow the subject to "self collect" their own samples for subsequent delivery to a laboratory for testing. Samples that are generally considered to be suitable for self collection comprise bodily secretions and exudates such as sputum, saliva, urine, feces, genital tract secretions, tears and sweat that can be obtained without penetrating the skin. Screening tests have long been performed on self collected urine and fecal samples, but only relatively limited use has thus far been made of the other above identified types of self collected samples at least in part due to logistics and cost issues associated with sample collection. Other issues that have hampered the adoption of self collection include the complexity and technique dependence of many of the available sample collection devices and methods and the potential for user error during the sample collection process.

The "standards of care" that define the targeted demographics and testing frequencies for various diseases within a population are basically consistent worldwide, but the rates of compliance with these standards can vary from under 25% to over 95% depending upon a number of factors. Resource limitations are a major contributor to this lack of compliance in the countries with the lowest compliance rates, but the inconvenience or difficulty associated with requiring subjects to present themselves at a designated location for sample collection is a significant factor in noncompliance in almost all countries. Yet another consideration is that in some relatively large populations religious and/or cultural practices discourage or forbid collection of certain kinds of clinical samples by medical professionals. Self collection of the requisite samples is seen as a way of addressing these issues, especially if the subject can send the sample directly to a laboratory or other designated location via a postal service, courier service or similar means.

The ability of a subject to order a clinical test on demand and to directly receive the test results has also recently become available. In this model the subject orders the test and receives the results via the Internet or other means of electronic communication. Although a few of these on-demand subject ordered tests utilize self collected samples, most require that the subject present themselves at a clinic, laboratory or other facility for sample collection by a medical professional. For economic, privacy and other reasons there is increasing interest in transitioning the majority of these on-demand tests to the use of self collected samples.

Numerous devices and kits such as those described for the self collection of clinical samples, but none have been successful due to the high level of skill required in order to obtain an acceptable sample; the high cost per result; operational complexity and other limitations.

There is therefore a need for a low cost, easy to use means for the self collection and transport of a clinical sample that can be widely deployed and can reliably be used by a subject who has had little or no training.

SUMMARY

The packaging for biological (e.g. clinical) samples and methods of self-collection of such samples addresses the need for low cost, simple to use high integrity packaging for the materials and supplies needed in the self-collection of subject samples and the delivery of such samples to a laboratory for testing or evaluation. There are many instances wherein self-collection is a necessity. Otherwise subjects may not be diagnosed and may succumb to adverse conditions that could have been treated. Subjects such as women whose religion forbids being touched by others, subjects at great distance from medical personnel, and the like.

A packaging for clinical samples includes:
  a flexible receptacle includes a primary reclosable sealing means;
  a reclosable support for a flexible receptacle, wherein the support comprises one or more additional sealing means for the receptacle; and
  wherein the one or more additional sealing means creates one or more pinch points in the flexible receptacle adjacent the primary reclosable sealing means.

The flexible receptacle may have primary reclosable sealing means that include a press seal, a zipper seal, a screw seal, or a snap seal. The one or more pinch points are adapted to prevent failure of the primary reclosable sealing means of the flexible receptacle. The flexible receptacle may contain a preservative in liquid or solid form. The pinch point is located between a substantial portion of the preservative and said primary reclosable sealing means. Failure of the primary reclosable sealing means of the flexible receptacle is prevented by limiting forces from the preservation applied to the primary reclosable sealing means by blocking a portion of the preservation from interacting with the reclosable sealing means at the pinch point. The packaging may include a second reclosable support, the second reclosable support enclosing the reclosable support.

In the packaging the second reclosable support further may include a provision for enclosing additional materials and/or supplies that are necessary and/or useful in the collection of the samples with reclosable support.

A method of packaging a clinical sample includes collecting the clinical sample on a collection device; placing the collecting device in a flexible receptacle, that includes a primary reclosable sealing means; closing the primary reclosable sealing means; placing the flexible receptacle in a reclosable support, the reclosable support including one or more additional sealing means; closing the reclosable support such that the primary reclosable sealing means of the flexible receptacle is outside the reclosable support; and creating a pinch point in the flexible receptacle through the one or more additional sealing means.

The method also may include a step of inserting a preservative in liquid or solid form into the flexible receptacle before closing the primary reclosable sealing means. The pinch point in the flexible receptacle is adjacent the primary reclosable sealing means.

DETAILED DESCRIPTION

Figure 1:
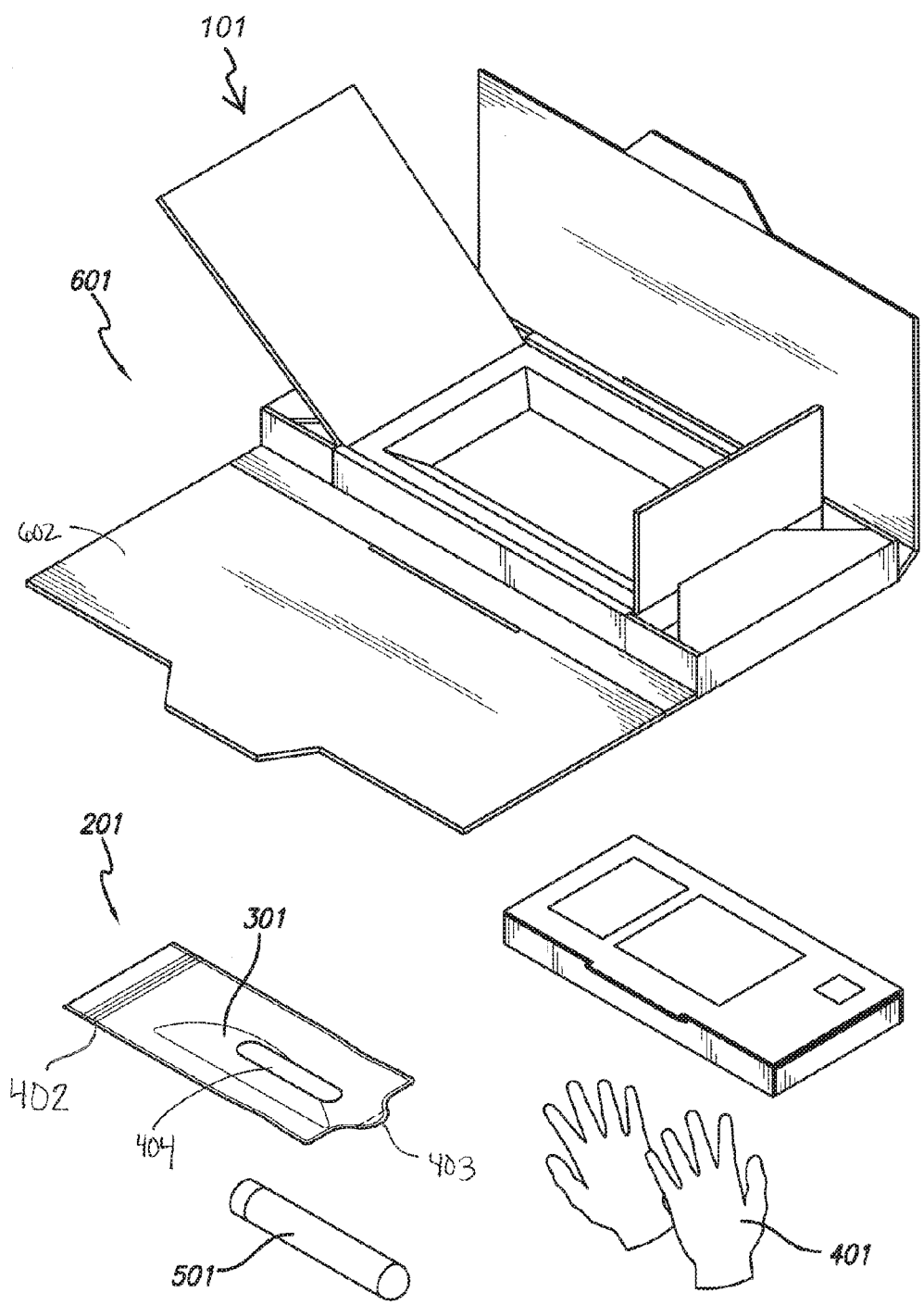
FIG. 1 is a diagrammatic view of the kit components.

A methods for self collection of a clinical sample must simultaneously meet a number of stringent requirements, for example:

Any such means must be capable of reliably providing an "adequate" sample comprising a sufficient amount of a material that is suitable in type, form and composition for use in the intended test(s). The criteria for sample adequacy are largely set by the test to be performed and in some cases is additionally defined by "standards of care" established by medical societies and other authorities.

The methods must provide a suitable collection device and must be capable of preserving the functionality and integrity of all devices, materials and supplies that are provided to the subject for use in sample collection during shipping and storage for at least one and preferably at least two years. In addition the means must provide for preserving the integrity of the collected sample for a period of time that can in some cases exceed 30 days.

The methods must permit successful use by a subject while requiring no assistance by medically trained personnel and with minimal, or preferably no, subject training or instruction. This encompasses aspects such as eliminating the need for the use of tools; minimizing the number of steps to be performed by the subject; ensuring that all steps performed by the subject are simple, familiar, intuitive, and not technique dependent; and providing features that prevent or mitigate subject errors. Furthermore, the means must be convenient for a subject to use in order to encourage compliance. Providing all necessary materials and supplies to the subject in the form of a kit improves convenience while minimizing the potential for errors caused by the subject providing inappropriate materials or supplies.

The means must minimize the total cost of collecting a sample and preparing it for testing or other evaluation. These costs include, but are not limited to the costs of all devices, materials and supplies; logistical costs including those related to the shipping, receiving and warehousing the means prior to dispensing; dispensing and delivery of the means to a subject; delivery of the of the collected sample to and receiving of the sample by a laboratory; and preparing the sample for testing or evaluation. The means must further be compatible with all available modes of transportation and delivery and must minimize the potential for error at each step in the logistics chain.

In order to be compatible with medical practices in various countries, the means must be medically, operationally and economically suitable for use on scales ranging from small private medical practices to national public health mass screening programs.

The methods must comply with all applicable laws, regulations and professional standards including, but not limited to those pertaining to medical devices; the environment, particularly with respect to packaging and waste minimization, allowed materials, and recycling and/or reuse; and various modes of transportation and shipping.

These considerations, which will be addressed more fully in the following descriptions and examples, are not adequately addressed by the devices and methods of the art, thereby limiting the utility and acceptance of the self collection of clinical samples. In addition, an increasing number of countries are implementing laws and regulations that are intended to control or contain healthcare costs. These cost containment efforts have traditionally focused upon the costs of the individual devices, materials and supplies used in sample collection in physicians office, clinic and hospital settings, but many of the current efforts are now focusing on the total "system" cost to obtain an analytical result and, as a consequence, are addressing the considerations such as those outlined above that have not been adequately addressed with respect to prior means for the self collection of samples.

Convenience kits and procedure trays, hereafter referred to as "kits", are known. Such kits are designed and intended to comprise most or all of the devices, materials and supplies that are needed in order to perform some specific procedure such as sample self collection in a single package that protects its contents during use, handling, transport and storage; and presents said contents to the user in an efficiently organized manner. In addition to logistical and convenience benefits, such kits reduce or eliminate the need for a subject to supply items for use in the procedure, thereby reducing the chances that the sample will be compromised through the use of inappropriate materials or supplies. These kits largely provide a sample collection device and a container for the collected sample, but do not comprise the complete set of features and functions that are needed to comprehensively address all of the requirements that must be satisfied in order for the kit to be successful.

A packaging system that combines sample collection devices, materials, components and methods in a unique manner that is specifically intended to meet the diverse and stringent requirements set forth above that pertain to the self collection of samples. This packaging system is adaptable to the self collection of clinical samples of various types for use in the detection, diagnosis and/or monitoring of many different disease states. The specific adaptations required for any given intended use are determined primarily by the requirements imposed by the specific test to be performed and are largely reflected in the dimensions and materials of construction of specific system components and in the composition of the preservative.

The Pap test, which was adopted as the standard of care for cervical cancer screening in the 1940's, will be used in the following descriptions and discussion as a representative example of the types of clinical tests that can be performed using self collection of samples. Other applications include collection of nipple aspirates and other biological samples which constitute a material shipped in suspension. The Pap test is instructive as it is one of, if not the most widely performed screening test world wide that can be performed using a self collected sample; it is performed on scales ranging from small private medical practices to very large national screening programs; and because, other than the use of different preservatives, the same self collected sample that can be used for cervical cancer screening also can be used for diagnosing and monitoring cervical cancer subjects; used in screening programs for sexually transmitted diseases and drugs of abuse; and used in tests for hormones, clinically significant metabolites, and other types of analytes of clinical interest. Thus the Pap test is a suitable example for illustrating the features, characteristics and benefits of the present invention. The considerations described and discussed below also apply to other types of non-invasively collected samples, sample collection devices and screening tests with only minor adaptations being required for their use within the scope of the present disclosure.

Collection Devices

The Pap test is based upon the morphological evaluation of cells collected from the uterine cervix. As it is known that over 95% of all cervical cancers originate in the transition zone region of the cervix, collection of cells from the transition zone and adjacent cervical epithelium is essential in order to obtain a valid test result. The position of the transition zone varies significantly in response to hormonal and other factors, thus requiring that a sample be collected from the entire region from the face of the cervical os to about 10 mm inside of the cervical canal.

The cells required for the Pap test are presently almost always collected by a physician or other medically trained individual using a spatula, broom, brush or similar device that mechanically scrapes, abrades or adhesively removes cellular material from the surface of the cervix. Numerous mechanical devices based upon similar principles have been proposed as means to allow a woman to self collect a cervical sample.

Washing or irrigating the cervix (lavage methods) with a "wash solution" (typically phosphate-buffered saline) and capturing the cells that become entrained in this solution has periodically been promoted for the collection of cells for Pap testing. The cell suspensions produced by this method are combined with a solid or liquid preservative before being sent to the laboratory for evaluation.

Dr. George Papanicoulau used surgical tampons and similar adsorbent devices to collect the necessary samples during his development of the Pap test. Samples collected using an adsorbent device comprise exfoliated cells which are cells that are naturally shed by epithelial tissue such as that which covers the cervix. The Draghi Diagnostic Tampon (U.S. Pat. No. 2,844,150) was subsequently developed specifically for the purpose of collecting exfoliated cells from the female genital tract. Numerous variants of the Draghi tampon, which comprise a rod-like adsorbent core enclosed in a porous covering, have subsequently been described. These include, but are not limited to various styles of tampons and to interlabial pads such as those described by Hirschman (U.S. Pat. No. 3,983,873), Gerstenberger (U.S. Pat. No. 5,575,047), and Olson (U.S. Pat. No. 5,916,205). In the tampon form these devices comprise a rod having a nominally circular cross section that is intended to be inserted into the vagina whereas the interlabial pad form is shorter in length; is intended to cover the entrance to the vagina; and typically has a "pinched" or otherwise shaped cross section that is intended to facilitate retention of the pad between the labia. An alternative form of interlabial pad described by Brown (U.S. Pat. No. 6,183,456) comprises a flat oval shaped adsorbent core having a porous or pervious covering on one face and an impervious covering on the opposite face. Both types of devices function by absorbing the secretions of the genital tract with the exfoliated cells entrained in these secretions being preferentially retained on the porous covering of the device.

In the case of the self collection of samples from the female genital tract, adsorbent sample collection devices best satisfy the previously set forth requirements.

One major aspect in this determination is that adsorbent devices inherently sample the entire genital tract including the cervical transition zone thereby ensuring that cells of the necessary types are collected even in the face of significant user error. This contrasts to mechanical and lavage methods that primarily collect samples from the exposed face of the cervix and require special features and techniques in order to ensure obtaining cells from the interior of the cervical canal where the transition zone is often located.

Another major aspect of this determination is that adsorbent devices, particularly in the forms of tampons and interlabial pads, used for sample collection are identical in both design and use to the corresponding devices that have long been used for sanitary purposes by women worldwide and are therefore familiar to the intended users. This familiarity with both the devices themselves and their use contributes significantly to satisfying the requirements for reliability and ease of use as well as to reducing the potential for user errors. In contrast, mechanical and lavage methods involve relatively complex unfamiliar procedures and require significant levels of skill, dexterity, attention to detail, and, in some cases, knowledge of cervical anatomy on the part of the user in order to ensure that an adequate and clinically useful sample is obtained.

Yet another aspect of this determination is that tampons and interlabial pads are inexpensive; well accepted by subjects, physicians and regulators; stable during storage and shipping; and due to their compact forms and light weights, relatively inexpensive to package, transport and warehouse. These attributes are shared with certain types of mechanical sample collection devices, most notably cervical spatulas and endocervical brushes, but other types of such devices such as exemplified by those identified above, are typically more expensive, bulky, heavy and often have limited shelf lives. The actual sample collection portion of a lavage type device can be relatively simple, but complex and expensive ancillary equipment such as pumps and reservoirs are required for their use.

Sample Recovery

After a sample has been captured by a collection device, it must be recovered in a form that is suitable for delivery to a laboratory.

The cells collected using mechanical devices such as spatulas and brushes have traditionally been recovered from the device by smearing the collected cells onto a microscope slide and then "fixing" them by application of a solution that simultaneously preserves the cells and adheres them to the slide. The slide with attached cells is then sent to a laboratory for evaluation. A similar method has been used with samples collected by an adsorbent device.

The so-called liquid-based preparation (LBP) is an alternative method that has long been used for the recovery of professionally collected non-gynecological samples such as fine needle aspirates and is increasingly being recommended by medical societies and national health authorities for the recovery of professionally collected cervical samples. In this method the cells are recovered in the form of a cell suspension by washing them from the cell collection device with a preservative solution. This suspension is then sent to a laboratory where the cells are deposited onto a microscope slide and evaluated. A separate fixation step is generally not required for LBP samples.

The LBP method can be practiced in two different ways. In one way the sample is recovered by agitating the collection device in the preservative solution; discarding the washed collection device; and sending the sample suspension to the laboratory. In the second way the collection device with attached sample is inserted into a container comprising the preservative solution and the container with enclosed collection device and preservative is sent to the laboratory. Agitation that occurs incidental to transport of the container results in the sample being washed from the collection device. The collection device is separated from the suspension in the laboratory and discarded.

Lavage samples are intrinsically collected as a suspension of cells in the wash solution. At a minimum these samples require the addition of a liquid or solid preservative before they are sent to the laboratory.

In the case of the self collection of samples from the female genital tract, the LBP method of recovery of the sample from the collection device by shipping the collection device to the laboratory in a container comprising the preservative solution best satisfies the previously set forth requirements.

One major benefit of the preferred form of the LBP method is that it minimizes the number and complexity of the steps that must be correctly performed by the subject, thereby providing ease of use and minimizing the potential for user error. This method also eliminates the need for the subject to dispose of a potentially biohazardous collection device after the sample has been recovered. Instead, disposal is performed in a laboratory by personnel who have the equipment and training needed in order to safely handle such materials. In contrast, successfully preparing a "smear" requires a certain level of technical skill and dexterity; requires that the smear be made and fixed immediately after cell collection in order to minimize degradation of the cells; increases the potential for the recovered sample to become contaminated. Smearing also requires that the subject handle and dispose of a collection device that has not been exposed to the disinfectant action of a preservative and is likely to be far more contaminated than the same device processed using a LBP method. Lavage methods can be configured such that the preservative is in the container used to capture the cell suspension, thereby reducing the number of steps to be performed by the subject. However, the large volume of sample suspension produced by this method must be handled and shipped by the subject and the subject must dispose of the collection device and dispose of, return or store the ancillary equipment used in this method.

Although Buck and others have described LBP-based means, some of which have utilized adsorbent devices, for the self collection of samples for Pap testing, these means have not been successful due to their failure to satisfy many of the other previously presented requirements pertaining to such means.

Preservatives

The preservative used in a LBP method is selected such that it is compatible with the tests and evaluation procedures that are to be performed on the collected sample by the laboratory. The preservative solutions used in the LBP process to preserve samples for evaluation using the Pap test typically comprise a 20 to 50% aqueous solution of one or more lower alcohols and may comprise additional components for purposes such as the dispersal of mucus; lysis of red blood cells and improvement of the adhesion of the sample to a microscope slide. One formulation of such a preservative is described by Hurley (U.S. Pat. No. 5,256,571) and largely comprises a 50% solution of methyl alcohol in a sodium acetate buffer of pH=5.6. Another group of formulations largely comprise a 20-30% solution of ethyl alcohol in a sodium acetate buffer while yet another group comprises mixtures of alcohols and other components such as described by Lorincz (PCT/US98/026342).

Certain LBP preservatives that are widely used in the art comprise in part an alcohol or other ingredient at a concentration that causes the preservative to be classified as toxic and/or flammable for regulatory purposes. In addition to presenting a risk to the subject, the regulations that apply to the shipping, handling and storage of materials that are classified as being toxic and/or flammable can significantly increase the costs of these activities and therefore increase the cost per result. A preservative solution that is compatible with the test to be performed, but is not classified as being toxic or flammable is therefore preferred.

Receptacle

Any means for the self collection of a sample must provide at least a receptacle that can be closed and sealed by the subject for the purpose of containing the collected sample during shipment to the laboratory. One or more additional receptacles may be provided for purposes such as containing a preservative or fixative during shipment to a subject. Alternatively the same receptacle may be used to deliver the preservative to the subject and the sample to the laboratory. Receptacles of the art largely comprise rigid body screw cap tubes, vials or bottles that may be provided as independent entities or may, in the manner described by Leet, be an integral component of the collection device. Screw cap conical bottom tubes (centrifuge tubes) and various types of medical sample shipping receptacles derived there from are commonly used sample transport while either screw cap vials or these conical bottom tubes are typically used for delivery of a preservative solution. Comparable tubes and vials having snap closures are also known in the art, but are less commonly used due at least in part to concerns about maintenance of seal integrity. Snap closures can, however, provide certain cost benefits and typically impose fewer constraints on design and form factor than do screw closures. In particular, the form of a screw closure approximates a hollow right circular cylinder. This form is appropriate for use with an rod-shaped collection device such as a tampon that has an approximately circular cross section, but it is volumetrically inefficient when used with a device such as a spatula or the interlabial pad described by Brown that has a thin rectangular cross section.

Although screw and snap closure containers are widely available and their use is quite familiar to subjects, they have certain limitations when applied to means for the self collection of clinical samples.

Screw and snap seal closures comprise two components: a removable closure element and a fitment that is part of the container to be sealed. Seals between these two components are formed by pressing one face of the closure against the mouth of the opening in the fitment and by the deformation of mating features such as screw threads in the closure and fitment. The forces required to cause this deformation are generated over an engagement length through torque applied to the screw threads or interaction between cam-like features in a snap fit arrangement. Although these features are required to deform, the remainder of the closure and fitment must be strong enough to resist the applied forces without significant deformation. The engagement length between the closure and fitment must also be great enough to allow development of sufficient force to establish the seals without exceeding the strengths of the materials comprising these components. The force required to engage or disengage a snap or screw seal is applied to the one part of the structure, typically the closure, while the other portion, typically the fitment, is held in a manner to resist this force. This means that some, if not all of the remaining portions of the receptacle must be strong enough to resist these forces. Screw and snap seal receptacles and particularly the closure and fitment portions thereof are therefore large and substantial structures comprising significant amounts of material. This large amount of material translates into a significant cost that, particularly in the case of a screw seal, is further increased by the complex high precision tooling required to form suitable threaded features. The size and weight of receptacles comprising a screw or snap closure also tend to increase shipping and other logistical costs.

The integrity of the seal created by a screw closure is sensitive to the amount of torque that is applied to the closure. If insufficient torque is applied, the sealing surfaces are not sufficiently deformed to create the desired seals whereas over tightening a screw closure can result in excess deformation that can impair seal integrity and can result in seal failure. Furthermore, if the closure is insufficiently tightened, it can loosen when exposed to vibrations such as may be encountered during shipping. The amount of torque that a subject applies to engage a screw seal must therefore be controlled to within relatively narrow limits in order to prevent leakage. Closures comprising a torque control mechanism are known, but are bulky and expensive. The increases in cost, size and potential for user errors associated with screw and snap seals are all inconsistent with the requirements for a means for the self collection of a sample as previously set forth. Screw and snap seals can, however, be used in the practice of the present invention under those circumstances where these limitations are acceptable.

The most common forms of screw and snap closures can be opened and closed multiple times. This allows the same receptacle to be used for delivery of a preservative or other material to the subject and delivery of the collected sample to the laboratory. Single use versions of these closures that cannot be reclosed once they have been opened are also known. Such forms are suitable for either delivery of a preservative or other material to a subject or delivery of a sample to a laboratory, but the subject cannot reuse the receptacle in which preservative has been received to ship the collected sample to the laboratory. This need for two separate receptacles increases the cost per result and introduces an opportunity for error as the subject is required to transfer the preservative from one receptacle to the other.

Some screw and snap seal receptacles provide for both a reclosable and a single use seal in a single structure. In these designs the single use seal generally comprises a membrane that is thermally, adhesively or otherwise bonded such as to completely occlude the opening in the fitment and such that the single use seal membrane lies between the fitment and closure of the reclosable seal. Alternatively, a neck band or similar means may be used to form a single use seal between the closure and the body of the receptacle. In some cases regulations pertaining to the shipment of liquids require that a receptacle comprising a screw or snap closure additionally provide for a neck band or similar means to ensure that the closure remains fully engaged during shipping. Depending upon the amount and nature of the liquid in a receptacle, these regulations may also require that the receptacle be further enclosed in an additional container so as to contain any leakage that may occur.

Other forms of single use receptacles such as hermetically sealed pouches and receptacles manufactured by a form-fill-seal (FFS) process are also known and may be used for purposes such as the shipment of preservative to a subject, but as resealing these types of containers requires the use of special tools and equipment, they are not suitable for use in shipment of a sample from the subject to the laboratory.

Although screw cap receptacles are reclosable, effective and widely accepted for the purposes identified above and have additional attributes such as their use being familiar to subjects; commercial availability from numerous sources; and in the case of conical bottom centrifuge tubes, compatibility with a means that is typically used in the laboratory to prepare self collected samples for evaluation, they do not adequately address the requirements set forth above that are imposed in the self collection of samples.

Many of the limitations of screw and snap seal receptacles can be overcome through the use of a receptacle comprising a reclosable press seal flexible pouch.

One reclosable flexible pouch that is used for the transport and short term storage of liquid samples is described by Mead (U.S. Pat. No. 2,973,131). After introducing a liquid into this pouch through its open end, this open end is sealed by rolling the end around an armature comprising two soft iron wires, these wires subsequently being folded to retain the end of the pouch in its sealed condition. This rolled seal suffices for the short term storage and transport of liquids having relatively low volatility, but is not adequate to contain a volatile liquid such as a preservative or when the receptacle is exposed to a pressure differential such as will occur if the filled pouch is shipped by air.

The form of reclosable flexible pouch described by Naito (U.S. Pat. No. 3,340,116) is used for a multitude of purposes including the temporary storage of liquids. The seal in this type of pouch is commonly referred to as a "press" or "zipper" seal comprising a male and a female member attached to opposite interior faces of the pouch. The male member in such a seal comprises a bulbous ridge that when pressed into a groove in the female member is captured and retained by complimentary features on the inner surfaces of the groove. The specific form described by Naito evidence one male and one female member, each of which is formed as an integral part of the pouch wall. Many variants of this basic form include forms having various male and female profile shapes; forms comprising multiple male-female pairs; forms that provide visible indication of proper engagement of the male and female members; and forms in which the male and female members are provided as strips that can be bonded to the material comprising the faces of the pouch.

If the end of the pouch bearing the seal members is designated as the top of the pouch, at least the sides and bottom edges of the pouch are sealed by bonding or more commonly fusing together the sheets of material comprising the faces of the pouch. In some cases these seals comprise a thin line wherein the sheets of material are joined approximately edge to edge. In other cases a wider "high integrity" seal is formed by joining the material in the seal area together face to face.

One limitation of the use of a press seal pouch for the storage and transport of a fluid is that the formation of leakage channels where the edge seals cross the press seal cannot be entirely prevented. The rate of leakage thorough these channels is, however, generally sufficiently low that such pouches can be used for the short term storage of liquids. The present invention provides means that permit these pouches to additionally be used for the long term storage and shipment of even volatile low viscosity liquids such as some preservative solutions.

A second limitation of the use of a press seal pouch for the storage and transport of a fluid relates to the expansion of air trapped within the pouch when the pouch is exposed to a reduced ambient pressure such as may occur during air shipment or alternatively the increase in the pressure within the pouch if it is crushed or heated. Both conditions can result in forces being applied to the pouch seals via the pouch walls that can result in seal failure. At one extreme these forces are shear forces that act in the plane of and are dissipated over the area of the seal. Forces acting at an angle to the plane of the seal result in peel forces that are concentrated along the line defined by the intersection of the front and back pouch faces and have a magnitude that is a function of the angle between these faces. As peel forces are concentrated along a line while shear forces are spread over an area, peel forces are more likely to result in seal failure. A feature of the present invention is that it limits the magnitude of these peel forces to less than the magnitude that can result in seal failure.

Other Components

In order to comply with shipping regulations the receptacle must typically be packaged in some manner. The minimum requirements that apply to this packaging are that it provide at least some designated level of protection for its contents; contain any fluid leakage that may occur; provide for labeling that at least identifies the shipper and intended recipient; and provides any warnings or cautions that may be appropriate to the contents of the package. The logistics related to the storing, shipping, dispensing and using the package and its contents; regulations pertaining to medical devices and environmental matters; and marketing considerations impose additional requirements that must also be satisfied by this packaging.

For logistical reasons, for the convenience of the subject, and to minimize the potential for errors it is desirable that all devices, materials, supplies, instructions and other items required by a means for the self collection of a clinical sample be packaged together and provided in the form of a kit. It is furthermore desirable that this kit be adaptable for the self collection of multiple types of samples. A kit that satisfies the requirements pertaining to a means for the self collection of a clinical sample is set forth in the following examples.

Examples are provided for illustrative purposes and are not intended to limit the scope of the disclosure.

EXAMPLE 1

Kit Composition

A kit for the self collection of a clinical sample will at a minimum comprise: a sample collection device; a preservative for the preservation of the collected sample during transport to the laboratory; instructions for use and other labeling that is required by law or regulation; and packaging for these items. The kit may also contain additional items as appropriate to the specific sample to be collected. An example of one such kit is illustrated in FIG. 1. This kit includes:

A sample collection device (301). An interlabial pad of the form described by Brown is shown in this Figure, but interlabial pads of other forms are suitable, tampons such as those described by swabs, brushes or spatulas of various forms; and other such devices may be used as appropriate to the requirements of the specific intended use of the kit. The collection device may be sterile or non-sterile as appropriate. The collection device is preferably contained within a separate pouch (not shown) or other protective packaging to prevent it from becoming contaminated or otherwise compromised prior to receipt by the subject.

Figure 3A:
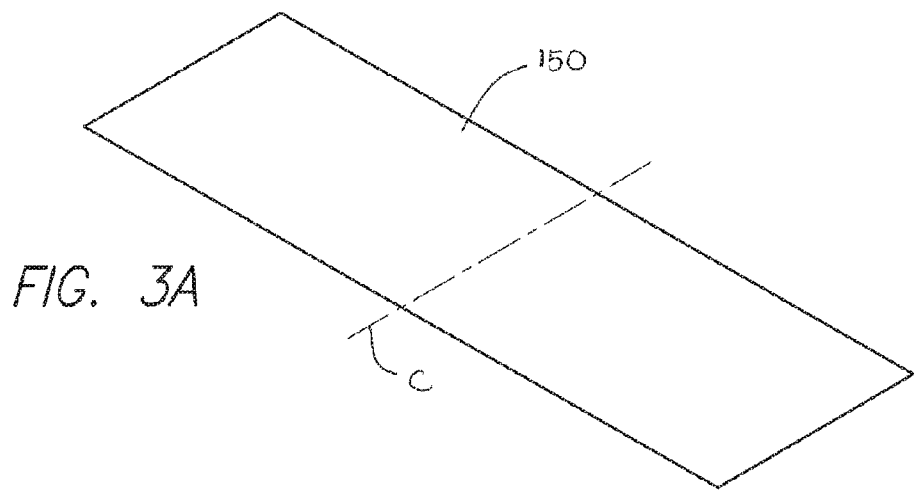
FIG. 3 is a schematic representation of a typical process for pouch fabrication.
Figure 3B:
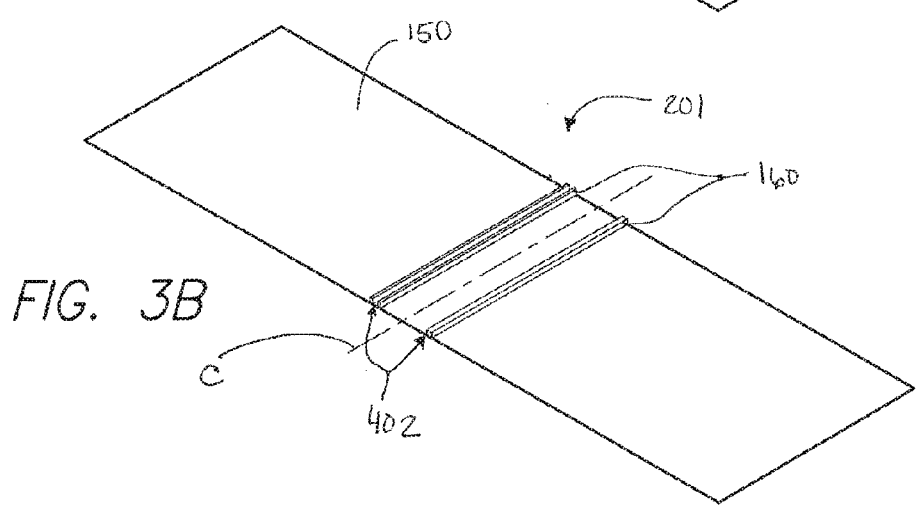
Figure 3C:
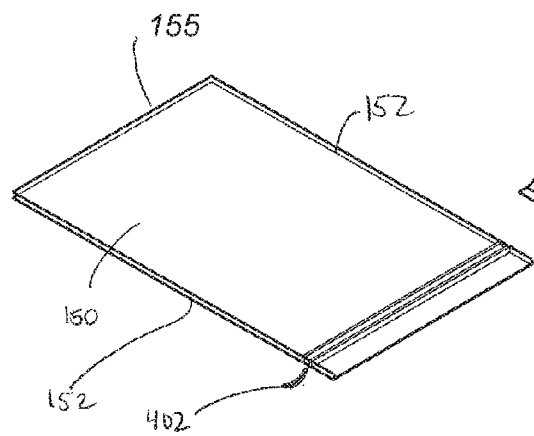
Figure 3D:
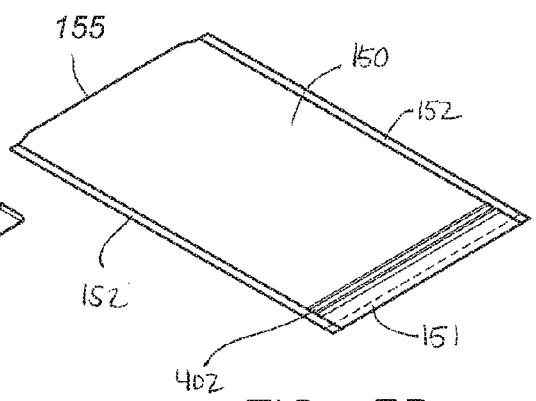
Figure 3E:
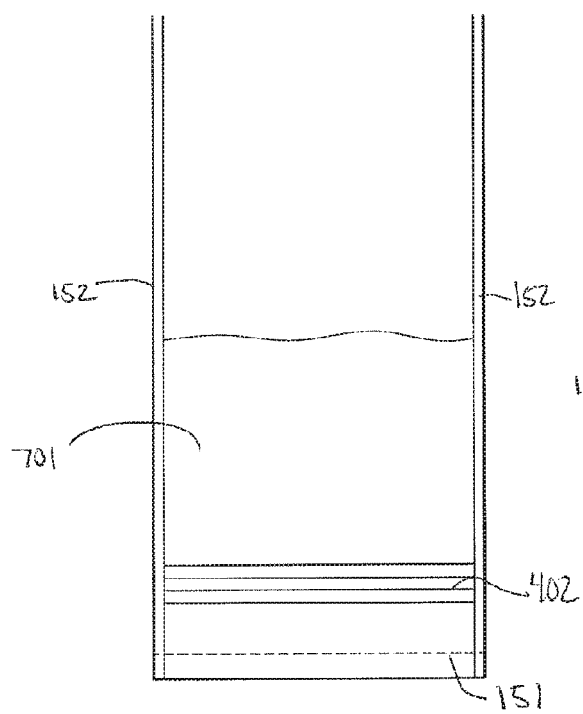
Figure 3F:
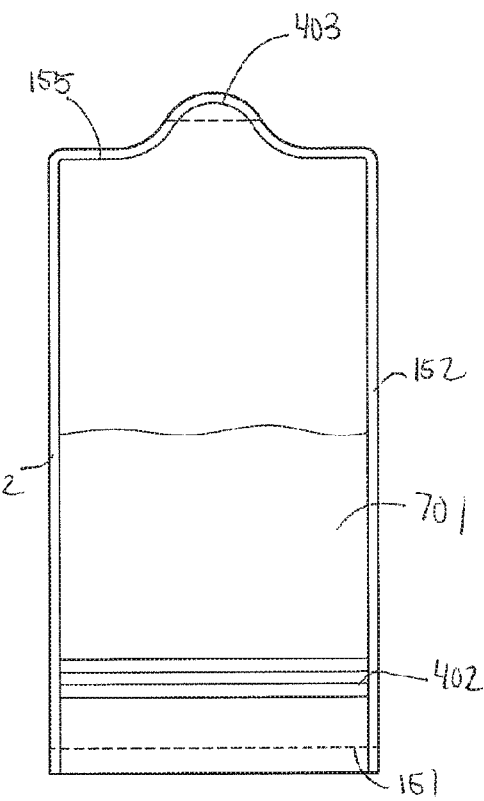
Figure 4:
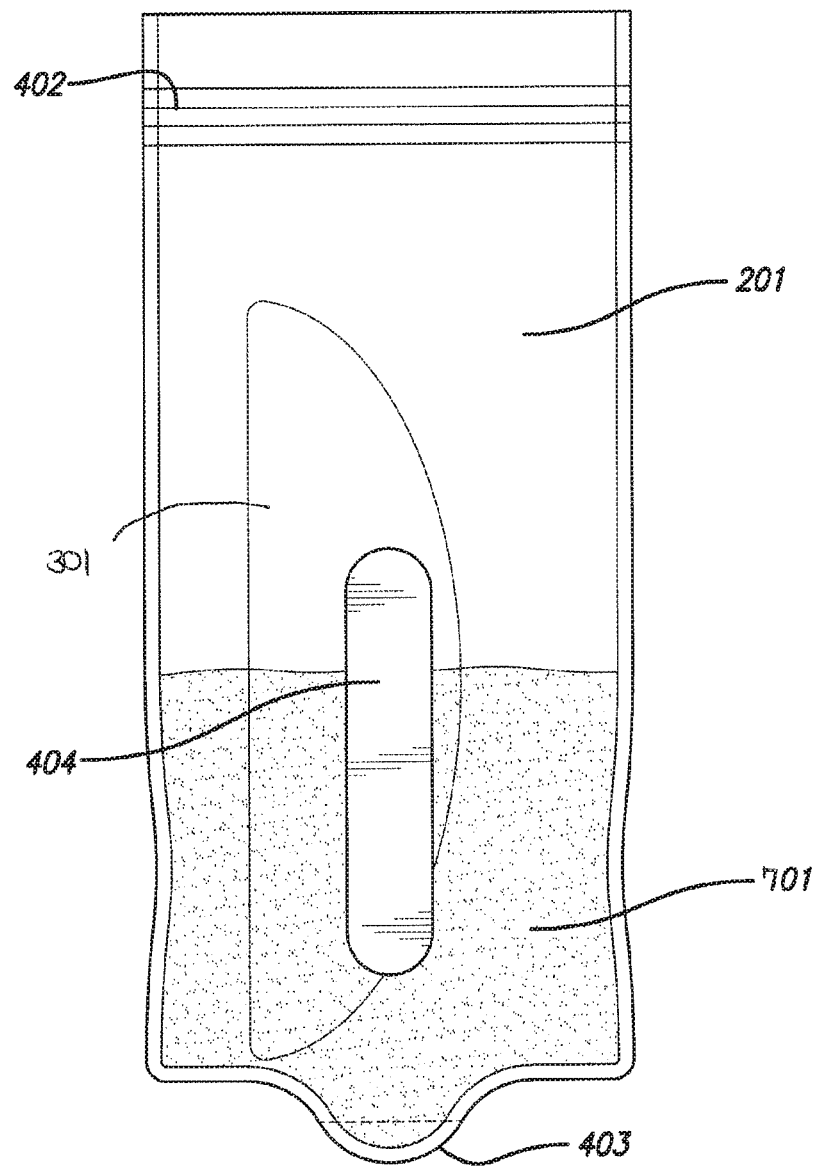
FIG. 4 is a diagrammatic view of a press seal pouch containing preservative solution.

A liquid for the preservation of the collected sample (701, as illustrated in FIGS. 3E, 3F and 4). The composition of this preservative liquid will depend upon the specific test or tests to be performed on the collected sample. Although such preservatives typically comprise an aqueous solution of one or more alcohols, each contains additional ingredients to optimize the preservative for use with a particular test. This preservative liquid must be packaged for delivery to the subject. In the preferred embodiment the preservative is contained in a receptacle (201) comprising a reclosable pouch that will subsequently be used to transport the collected sample to the laboratory.

In an alternative embodiment the preservative is packaged in a separate single use container (501) such as a snap-seal form-fill-seal (FFS) vial or a tear-seal pouch. This alternative is desirable in those cases where the kit is expected to be exposed to particularly adverse conditions and may be useful when otherwise identical kits are to be assembled on demand for the collection of samples that are to be used in different tests. Two disadvantages of this alternative embodiment are that it requires additional materials and materials handling, thereby increasing the cost of the kit; and it requires that the subject transfer the preservative from the container in which it is received into the receptacle used to ship the sample to the laboratory, thereby increasing the potential for error. An additional consideration is that an increasing number of laws and regulations encourage or mandate the minimization of the use of packaging materials and/or limit the types of materials that may be used in such packaging.

Each package of separately packaged preservative solution is typically required by regulation to be labeled (404) to at least identify the nature and amount of the package contents; to identify the lot and date of manufacture; and to provide any warnings and/or cautions that may be applicable. As set forth below additional labeling may also be necessary or desirable Packaging for the collected sample during transport to the laboratory. In the preferred embodiment as illustrated in FIG. 1, this packaging comprises a flexible receptacle (201) having a reclosable press seal (402) and optionally, but desirably, comprising a "tail" (403) or similar feature to facilitate recovery of the sample in the laboratory. Flexible receptacles that incorporate a reclosable screw or snap seal are within the scope of this invention, but are not preferred due to the increased costs associated with these types of closures and their greater heights than the preferred press seal which necessitate increasing the physical dimensions of the kit. It is desirable that kit dimensions be minimized for cost and logistical reasons.

Packaging to comply with shipping regulations and to ensure the integrity of the kit and sample during transport. Specific regulations apply to the packaging of liquids in general and to the packaging of biological samples and potentially hazardous liquids in particular for transport. The requirements imposed by these regulations depend in large measure upon the mode of shipment and the nature, amount and type of the liquid. As the kits and/or samples of the present invention are likely to at some point be transported by air, compliance with the air transport regulations, which are generally more restrictive than for those pertaining to other modes of transport, is required. In addition to requirement for crush and penetration resistance, these regulations require that at least two sealing means and a means of containing any spills or leaks that may occur be provided. For the purposes of self collection of clinical samples this secondary packaging should be low cost, compliant with the applicable shipping and environmental regulations, and designed to minimize the chances of user error. In the present invention these requirements are met by the reclosable support (101) shown in FIG. 1.

External shipping packaging. External shipping packaging is intended to protect its contents during shipment; facilitate the logistics of shipping, handling, warehousing and distribution; and to provide the panel space that is required in order to comply with the various regulations pertaining to product and package labeling. The external packaging (601) illustrated in FIG. 1 satisfies these requirements for individual kits. Additional levels of external packaging that combine multiple packaged kits into shelf packs, cases and similar units are not illustrated and can be addressed in accordance with established industry practices.

Package inserts and/or other items. As described with respect to external package (601), it is preferred that all required warnings and cautions as well as the instructions for the use of the kit be on the external package. In many geographic regions it is additionally desirable, if not mandatory, to provide these and other information items in multiple languages. As the external package may not have sufficient surface area to accommodate all of this information in all required or desired languages, a separate package insert (602) containing this information may be included in the kit. Other items such as separately packaged preservative (701), applicators and/or gloves (401) may also be included in the kit if appropriate to the type of sample to be collected.

EXAMPLE 2

Sample Collection Device

The preferred collection device for routine self collection of a gynecological sample comprises a thin approximately oval shaped interlabial pad having a fluid absorbing core, a front sheet that is pervious to fluids and a back sheet that is impervious to fluids. A suitable interlabial pad of this type is described by Brown and are commercially available under the "Always Active®" (Proctor & Gamble), "InSync®" (A-Fem Medical), and other trade names. Other forms of interlabial pads and tampons, which generally have higher fluid absorption capacities than the preferred pad, may be appropriate if the flow of gynecological secretions is high. Suitable tampons are commercially available under the "Always Active®" (Proctor & Gamble), "Tampax®" (Tampax), and other trade names. Samples collected using an absorbent device contain materials including exfoliated cells, hormones, metabolites, microorganisms and the like, from the entire genital tract and can be tested for a wide variety of analytes. In those cases where a sample from a specific portion of the genital tract or from another anatomical site is required by the test to be performed on the sample, the use of a swab, wipe, brush, spatula, scraper or other device that is suitable for localized sample collection may be more appropriate and is accommodated within the scope of this invention. Alternatively, the laboratory can in some cases use biological markers and similar means to differentiate between sample constituents from different sites.

Under normal flow conditions it is typically necessary for the subject to wear the interlabial pad or tampon for approximately four hours in order to ensure that sufficient sample for testing has been collected. In some cases it may be necessary for the subject to interrupt sample collection before a sufficient quantity has been collected. As it is generally undesirable for the subject to resume sample collection using the same device, it may be appropriate to include a second sample collection device in the kit. In these instances both collection devices can be sent to the laboratory in the same container of preservative solution.

EXAMPLE 3

Preservative

The preferred preservative solution for use in this invention is determined by the requirements of the specific test or tests to be performed upon the collected sample. Preservative solutions that are suitable for use in this invention and that are compatible with the more prevalent tests are commercially available from many suppliers including, but not limited to those from Cytyc (ThinPrep®, PreservCyt®), TriPath (SurePath®), Cell Solutions (Synermed®), Digene (STM®) and others. Proprietary preservative solutions that are specifically intended for use with particular tests manufactured by specific suppliers are also commercially available and may be used if appropriate. Almost all of the suitable commercially available preservative solutions are comprised of a buffered aqueous solution of one or more low molecular weight alcohols plus various additives to impart specific characteristics to the particular product. The predominant formulations that are commercially available are comprised of an approximately 25% solution of ethyl alcohol in a pH=5.6 sodium acetate buffer or an approximately 50% solution of methyl alcohol in the same buffer. Some of the other available formulations include isopropyl or butyl alcohol, either as the sole alcohol or as a mixture with ethyl or methyl alcohol. The additives incorporated into these preservatives, which vary between brands, perform roles ranging from lysing red blood cells and preventing the precipitation of hemoglobin to suppressing microbial growth and improving adhesion of cells contained in the sample to a microscope slide. In some cases such as urine samples wherein the desired sample is a liquid, a solid preservative such as sodium azide that dissolves in the sample may be more appropriate than a liquid preservative. A solid preservative that is suitable for a particular type of sample may be provided to the subject in the same manner as the liquid preservatives previously set forth.

EXAMPLE 4

Receptacle

Receptacle Material:

The preferred receptacle for the preservative and collected sample comprises a flexible pouch having a press (zipper) seal closure. Although flexible press seal pouches are an almost ubiquitous item of commerce, few if any of these commercially available pouches are suitable for use in the practice of this invention. In particular the pouches used in the practice of this invention must meet unusually stringent requirements for seal integrity and materials compatibility.

With respect to materials compatibility, the materials used in the construction of the pouch must:

not absorb, dissolve, or otherwise bind any sample constituent that is to be tested for.

not release any substance that can degrade the sample or interfere with the testing to be performed on the sample.

not dissolve in or contain any materials that are leachable into the preservative solution.

have a permeation rate for the preservative and its constituents that is sufficiently low that it ensures an acceptable shelf life for the preservative and for the sample contained in the preservative when stored under the usual range of conditions encountered in commerce.

have at least the mechanical strength and other physical properties needed to meet the applicable requirements for pouch durability, flexibility and other characteristics.

be mutually compatible at least to the degree where the pouch components can reliably and durably be bonded together.

Press seal flexible pouches are predominantly manufactured from plastic film (150) comprising a single type of polymer such as polyethylene. Typical film thicknesses range from about 1 mil (0.001") in light duty pouches to as much as 10 mils in those intended for heavy duty use. Although pouches comprised of a single polymer can be made to satisfy most of the above requirements, the permeation rate of the preservative constituents through even the thickest single material film that is practical for use in a flexible pouch is sufficiently high as to limit the shelf life of the preservative in such a pouch to significantly less than the minimum required by a means for the self collection of clinical samples.

Films comprising multiple layers of different polymers are known in the art and can be constructed such as to have a permeation rate for selected molecular species that is significantly less than that for a comparable thickness of any of the individual polymers comprising the multilayer film. The choice of polymers comprising these layers, the thicknesses of the individual layers, the number of layers and the order of the polymer layers are some of the significant factors in determining the permeation properties of the composite film. By way of example, the alcohol and water permeation rates through a three layer structure comprising a middle layer of poly-(acrylonitrile) (PAN) or poly-(ethylvinylalcohol) (EVOH) between outer layers of poly-(ethyleneterephthalate) (PET) are sufficiently low as to permit a film having this structure to be used for the medium term packaging of solutions of alcohol in water whereas the permeation rate of water or ethanol through a single layer of comparable thickness comprising any one of these polymers is sufficiently high as to limit its use to no more than short term storage. In addition to their properties as a permeation barrier, the layers of PET in this exemplary structure also provide the significant levels of strength and stiffness that are desirable for the protection of the contents of a pouch, but may make the pouch too stiff for a subject to easily open.

The thicknesses of the PET layers and therefore the stiffness of the resulting pouch can be significantly reduced if a layer of a metal or a glass, which have barrier properties that far exceed those of most polymers, is introduced into the film structure in addition to or as a replacement for the intermediate PAN or EVOH layer described above. One such suitable structure comprises an aluminum foil laminated between two thin films of medical grade PET or another polymer. The free standing metal foils used in this lamination process may, however, may introduce an unacceptable degree of stiffness into a pouch.

Figure 2:
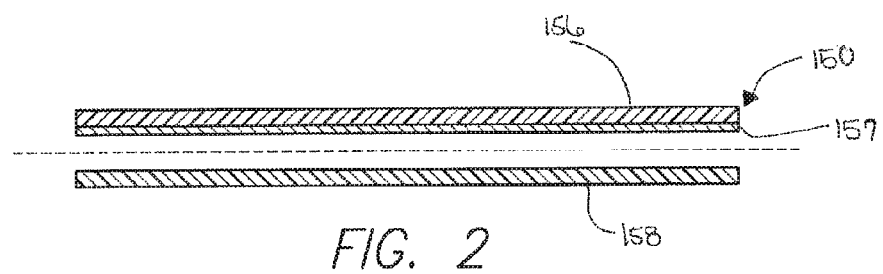
FIG. 2 is a cross sectional view of a multilayer film structure.

To preserve the flexibility of the pouch, a preferred structure for a film to be used in the fabrication of the receptacle of this invention comprises a thin (typically 48 gauge/0.5 mil) film of amorphous PET or PET-G (156), that has been vacuum metallized on one surface with 500-1000 Angstroms of aluminum (157) and then laminated to a 2-3 mil film of polyethylene (PE) to form a PE—adhesive—aluminized PET structure (158). Other types of polymer films such as polyesters or cyclic olefin copolymers may be used in place of PET and/or PE in this type of structure. By way of example, a structure comprising reverse-printed polyester—adhesive—aluminized polyester—adhesive—PE may be employed. Alternatively, the aluminum layer can be replaced by a layer comprising approximately 500 Angstroms of silicon dioxide, aluminum oxide or another glass that is deposited by reactive PVD or PECVD onto the PET film. This replacement provides barrier properties comparable to those provided by aluminum in a form that is useful if a transparent or translucent receptacle is desired. Other multilayer film structures may be used as appropriate to the particular preservative to be contained within the receptacle. The acceptable loss rate due to permeation depends upon the composition of the specific preservative and the requirements of the test to be performed, but will typically be less than about 1% of the weight of the preservative per year at 40° C. A typical film structure is illustrated in FIG. 2. As this loss rate is additionally a function of the surface area of the pouch, it is desirable to minimize the pouch dimensions.

Receptacle Fabrication:

The selected barrier film can be converted into reclosable press seal flexible pouches by any suitable method. By way of example, the receptacle used in the practice of this invention is most conveniently fabricated in the bottom fill (open bottom) format from a single web of film, but a top fill format and/or a two web process can be used with equal effect. Bottom fill pouches are generally more convenient if the preservative is to be shipped to the subject in the receptacle while the top fill format may be more convenient if the preservative is to be shipped in a separate container. A single web process for forming, filling and sealing a bottom fill pouch in a "1-up" configuration will be described and is illustrated schematically in FIG. 3. The actual process details will depend upon the specific manufacturing equipment that is available. Descriptions of alternative processes may be obtained from numerous sources.

The exemplary receptacle is fabricated from a web of the appropriate multilayer film stock (150) having a width that is equal to twice the overall finished height of the receptacle plus allowances for material handling and for trimming losses. The press seal (402) is most conveniently provided on a roll comprising a fully engaged male and female elements (160), each element having the selected number of seal features and, if desired, additional features such as an indicator for proper seal engagement. The web is folded in half lengthwise along its centerline C to form a C-shape; the seal strip is inserted into the throat of the C at a distance from the fold sufficient to allow for the addition of a perforated tear feature (151); and each element of the seal strip is bonded to the adjacent film surface. An optional line of perforations parallel to the press seal and between the press seal and the fold to permit the subject to open the receptacle without having to resort to a cutting tool may also be added at this time or in a later step. These perforations are preferably formed using a heated knife perforating tool that simultaneously creates the perforations and fuses the two sheets of film together around the periphery of each perforation thereby maintaining the integrity of the seal in the region between the press seal strip and the fold.

The edge seals (152) that define the width of the receptacle are then formed. The preferred edge seal for receptacles to be used in the practice of this invention is commonly referred to as a "high integrity" seal. This is a face seal that is created by fusing or bonding together the layers of film that form the front and rear faces of the finished receptacle along a line that can range from approximately 1/16 to over 1/4 inch wide depending upon the requirements for seal strength and integrity. These seals are preferably formed by thermally welding the two sheets together using a heated die or roller, but can also be formed using ultrasonic welding or by adhesive bonding. The web may be separated into individual receptacles concurrently with formation of the edge seals or in a separate step either before or after filling depending upon the design of the manufacturing machinery and the manufacturing process flow. The previously mentioned perforations between the press seal and fold may also be added at this time.

The edge sealed receptacles are delivered to the filling machine; oriented vertically with the bottom end up; opened; and filled with the desired volume (or weight) of preservative solution. In the case of an adsorptive sample collection device such as a tampon or interlabial pad, the preferred preservative volume is typically between two and three times the fluid uptake capacity of the device to ensure adequate recovery without excessive dilution. The preferred volume for a non-adsorbent sample collection device needs to be at least sufficient to recover the sample from the device, but is otherwise determined largely by the volume of sample required by the test to be performed on the sample. The bottom high integrity end seal (155) and, if desired, the tip feature (403) used to facilitate sample recovery in the laboratory are then formed using a heated or ultrasonic die that may also create an optional line of perforations across the tip feature to permit it to be opened in the laboratory without tools. If not done previously, the receptacles are separated into individual units using a knife or cutting die and then presented for inspection, labeling, and packaging. At a minimum, labeling comprises identification of the contents of the receptacle; the lot number; the filling or expiration date; and a unique serial number that allows each filled receptacle to be tracked in accordance with the pertinent regulations and to be associated with a particular subject and test result.

If the preservative is to be delivered to the subject in a container other than the receptacle, the receptacle can be made as described in the previous paragraph except that the filling step is omitted and the fill or expiration date is not included in the labeling on the receptacle.

A completed press seal receptacle with preservative is illustrated in FIG. 4.

EXAMPLE 5

Separate Preservative Container

If the preservative is to be shipped to the subject in a container other than the receptacle, the preferred container comprises either a multilayer pouch with a single use tear seal, the pouch material having an aluminum foil inner layer such as described in Example 4, or a single use form-fill-seal vial incorporating a snap seal. Both packages are articles of commerce and will not be further described.

EXAMPLE 6

Receptacles Incorporating a Screw or Snap Closure

Although not preferred, receptacles incorporating a screw or snap seal may be used in the practice of this invention. Due to the intrinsic circular symmetry of its opening, a screw closure is best suited for use with tampons and other collection devices that have an approximately circular cross section, but these closures are volumetrically inefficient when used with devices such as the interlabial pad described by Brown that have a high aspect ratio rectangular cross section. Within fairly broad limits snap closures may be designed to accommodate most types and styles of collection devices in a reasonably efficient manner. The utility of these types of closures is, however, somewhat limited as previously set forth. Additional limitations may apply depending upon where and how the fitment is attached to the pouch.

Screw and snap fitments may be attached to either the face or end of a receptacle pouch. Receptacles having a fitment on one face are relatively simple to manufacture, but the presence of the back face of the receptacle in close proximity to inside opening in the fitment can interfere with insertion of the collection device into the receptacle. Fitments can be attached to the end of a receptacle in either of two basic ways. In the simpler of the two approaches a nominally tubular receptacle is attached by thermal welding or other means to a fitment that has a tubular neck with a circular, eye-shaped or oval cross section as appropriate to the collection device. The bottom of the receptacle is then formed and sealed as previously described. In the preferred, but more complex approach, the receptacle is initially formed as an open top, flat bottom gusseted bag and the neck of the fitment terminates in a flat flange that is larger in extent than the maximum projected cross section of the body of the fitment. The flanged fitment is inserted from the inside of the bag through a hole in the bag bottom and thermally or ultrasonically welded in place. The fitment end of the bag is then folded flush with one face of the bag and open end of the bag is then closed, formed and sealed as previously described. In either of these processes, if the preservative is to be shipped to the subject in this receptacle, the preservative may be added to the receptacle before the open end of the receptacle is sealed or the open end many be sealed and the receptacle then filled through the fitment.

EXAMPLE 7

Support

Figure 5:
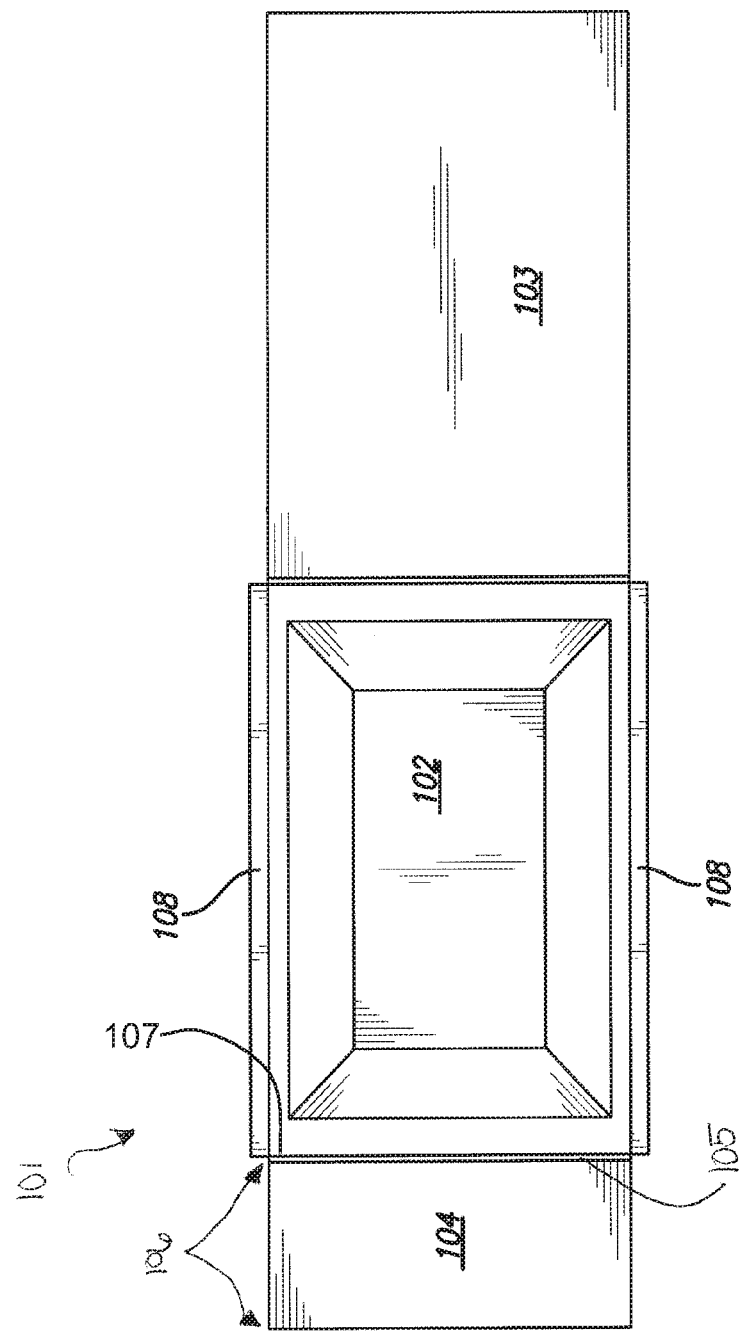
FIG. 5 is a top view of a support in its open state.

Fabrication:

A support (101) for use in conjunction with a press seal receptacle (201) such as is described in Example 4 is shown in FIG. 5. The support comprises an open faced tray (102) having a recess in which a portion of the receptacle may rest and be contained; a sealing surface (105); and two cover sections (103, 104), one cover section being hingeably attached to each end of the tray section. This support may conveniently fabricated by injection molding, thermoforming or similar means. The material selected for any specific sample collection application should be compatible with the preservative solution to be used and should be sufficiently flexible to permit the implementation of hinges and snap latches, but rigid enough to perfect the pinch seals described below. Non-plasticized materials are preferred and PVC-based materials are not recommended due to regulatory restrictions. Preferred materials for injection molded supports include a polyolefin such as PE, HDPE or PP while preferred materials for thermoformed supports are high impact polystyrene (HIPS), PET or ABS. A thermoformed support formed from 0.045" (nominal) HIPS sheet has, by way of example, been found to be suitable for use in the practice of this invention with most alcohol-based cytology preservatives. These supports conform to environmental regulations with respect to being made of allowed readily recycled materials and of being sufficiently durable that they can be cleaned and reused. An adsorbent pad or material may additionally be included in the tray portion of the housing if such a pad is required in order to comply with the applicable shipping regulations.

In addition to protecting the receptacle from penetration and crushing and providing containment for any fluid leakage that may occur from the receptacle, the support also provides multiple means of preventing fluid leakage from the receptacle, such means comprising at least multiple pinch seals and a means of ensuring complete engagement of the press seal. In the preferred embodiment illustrated in FIG. 5, one or more pinch seals (106) spanning the full width of the receptacle are formed by the engagement of sealing features located on the sealing surface (105) with mating features on cover 1 (104); and a pinch seal spanning the full width of the receptacle is formed by capture of the receptacle between the end of cover 1 (103) and the hinge (107) connecting cover 2 (104) to the tray section (102) of support (101); and the press seal of the receptacle is captured between cover 1 (103) and cover 2 (104), the features (108) (shown as the "bump outs" typically used for this purpose in thermoformed supports) latching the covers in their closed positions being arranged such that these latching features cannot engage the covers unless the press seal is completely engaged; and one or more pinch seals spanning the full width of the receptacle are formed by the engagement of sealing features (not visible in FIG. 5) located on cover 1 (103) with mating features on cover 2 (104).

These sealing functions provided by the support enable a receptacle in the form of a press seal pouch to contain a low viscosity volatile liquid such as a preservative for an extended period of time and reduces the chances that user error will compromise the integrity of a self collected sample being sent to a laboratory.

Figure 10:
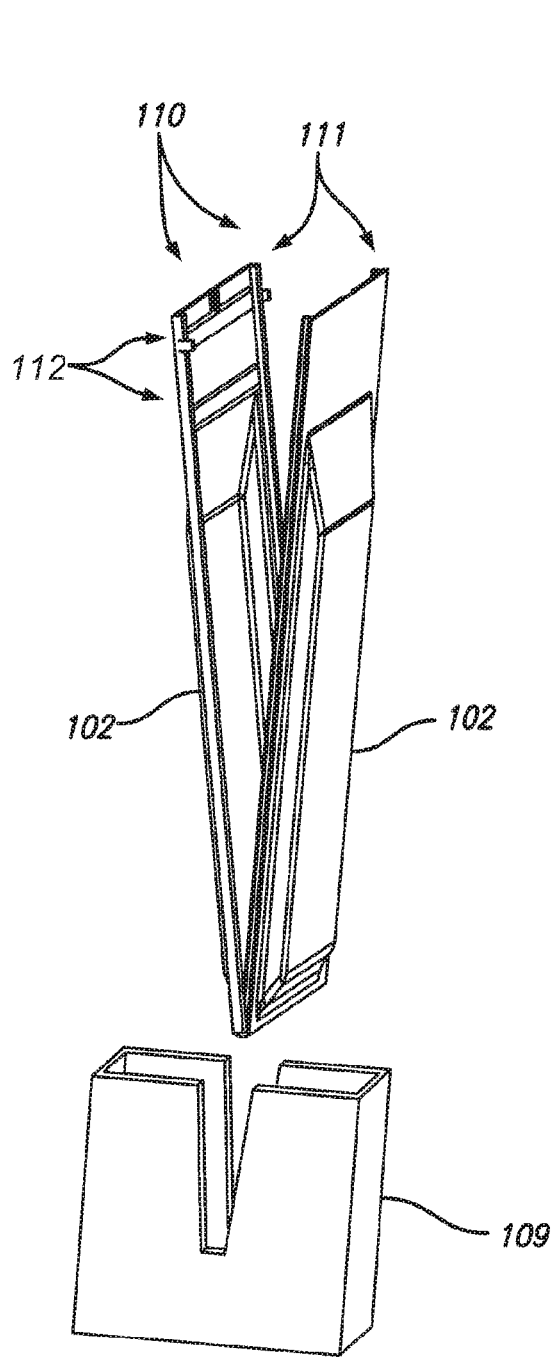
FIG. 10 is a diagrammatic view of an alternative support in its open state.
Figure 11:
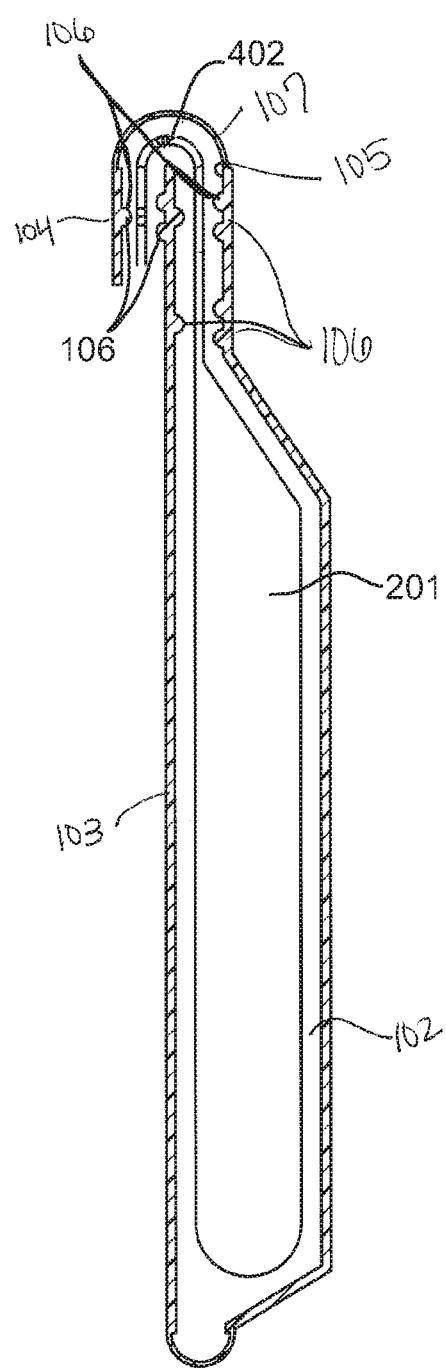
FIG. 11 is a cross-sectional view of the support of FIG. 5 in a closed state.

Another embodiment of the support comprising a clamshell structure having two pinch seal features (112) is illustrated in FIG. 10. This embodiment also comprises a removable base (109) that permits the housing to stably stand in a vertical orientation on a horizontal surface and hook features (111) that permit the receptacle to be suspended with its press seal in the open state to facilitate introduction of the sample collection device.

Use of the Support

Figure 6:
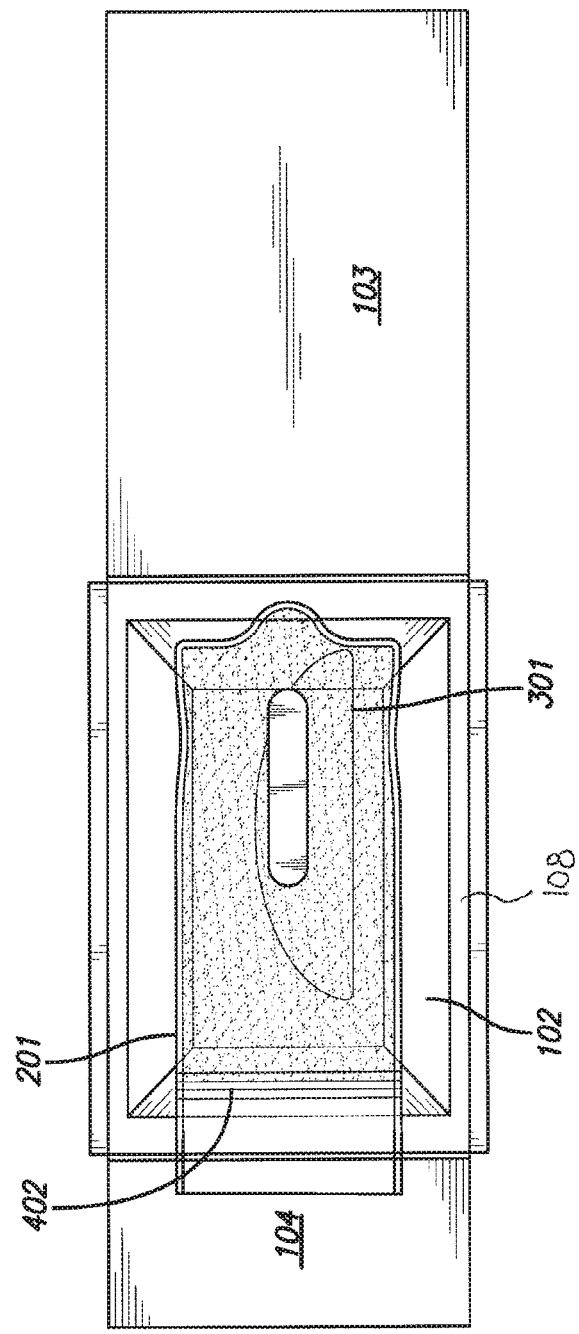
FIG. 6 is a diagrammatic representation of a pouch in an open housing.

As illustrated in FIG. 6, a receptacle containing preservative is prepared for shipping to the subject or prepared for shipment of a sample to a laboratory by placing the receptacle (201) in the tray portion (102) of the support such that the bottom portion of the receptacle, which contains substantially all of the fluid and the collection device (301) if present, is located in the tray portion of the support and the press seal portion of the receptacle is lying on top of the cover 2 (104). Closing cover 1 (103) encloses the body of the receptacle within the tray portion of the support and forms one or more pinch seals across the full width of the receptacle. Closing cover 2 forms a pinch seals between the end of cover 1 and the hinge section of cover 2 across the full width of the receptacle. Engaging the latch features (108) that retain covers 1 and 2 in their closed position captures the press seal (402) of the receptacle between these two covers in a manner that ensures that the press seal has been fully and completely engaged and concurrently forms an additional pinch seal across the full width of the receptacle between mating features on the two covers. Other types of latching features may be used as appropriate to the design and method of fabrication used in the manufacture of the support.

Additional Features of the Support:

The cross sectional profile of the tray portion of the support is additionally constructed such as to limit the range of angles that can be formed between the plane of the edge, bottom and press seals and the front and rear surfaces of the receptacle, thereby limiting the peel forces resulting from, by way of example, expansion of the air trapped in the receptacle during air shipment to levels that are significantly below those required to cause seal failure. Limiting these angles to less than about 75 degrees is generally sufficient if the preferred high integrity edge and bottom seals are employed, but may be reduced if a less durable seal type is selected. The internal dimensions of the tray section are largely determined by the dimensions of the receptacle and the volume of preservative contained therein.

The support may additionally comprise figures and/or other indicia that instruct the subject in the proper manner of using the support and/or providing the information needed for the efficient reuse and/or recycling of the support.

Although not preferred for reasons previously set forth, the support may be adapted for use with receptacles having screw or snap closures. The most significant adaptations required to this end include: increasing the dimensions of the sealing surface (105) such that the extent of this surface is consistent with the dimensions of the fitment employed; forming a hole or well in the extended sealing surface to accept the closure; preferably providing a complaint pressure pad on the portion of the surface of cover 1 that overlays the opening in the fitment; and rearranging any pinch seals that may be provided as dictated by the design of the specific fitment. Other adaptations may be required or appropriate in specific instances, particularly if the receptacle incorporates gussets.

EXAMPLE 8

External Packaging

Figure 7:
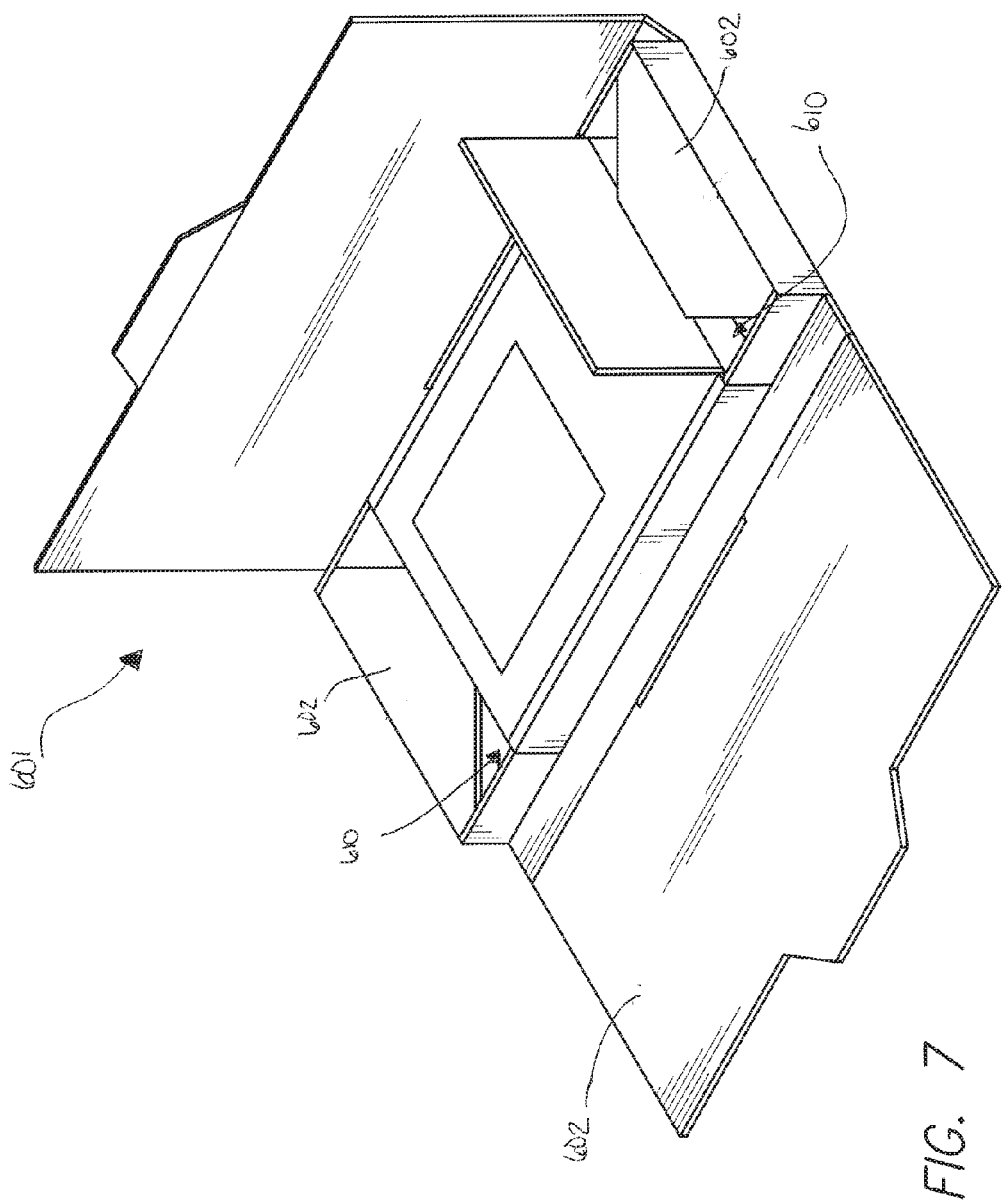
FIG. 7 is a diagrammatic view of a kit and its contents.
Figure 8:
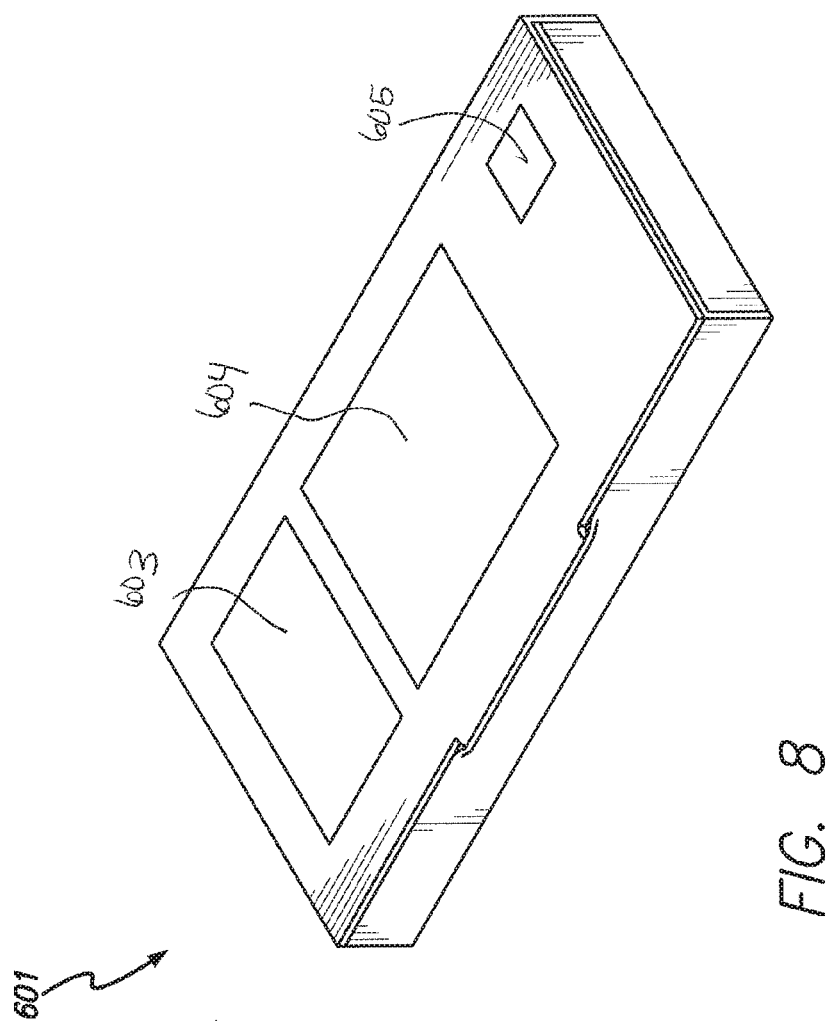
FIG. 8 is a diagrammatic representation of a kit that has been closed to expose the subject address information.

As previously set forth, all of the devices, materials, supplies and other items that are required for a subject to self collect a sample and deliver said sample to a laboratory are desirably packaged together in a single container and provided to the subject as a kit. An embodiment of a container that satisfies the numerous requirements that pertain to the packaging of a kit for the self collection of a clinical sample is illustrated in FIG. 7. In this embodiment the container is in the form of a foldable carton that may comprise solid bleached sulfite (SBS) card stock, typically of between 0.016" and 0.026" caliper, or other suitable material. In its folded state this carton encloses, protects and organizes the contents of the kit and gives the packaged kit the rectangular solid form factor that is preferred in conjunction with higher level packaging, distribution, and individual kit shipping. To minimize costs, the same carton is intended for both delivery of the kit to the subject and delivery of the collected sample to the laboratory.

Figure 9:
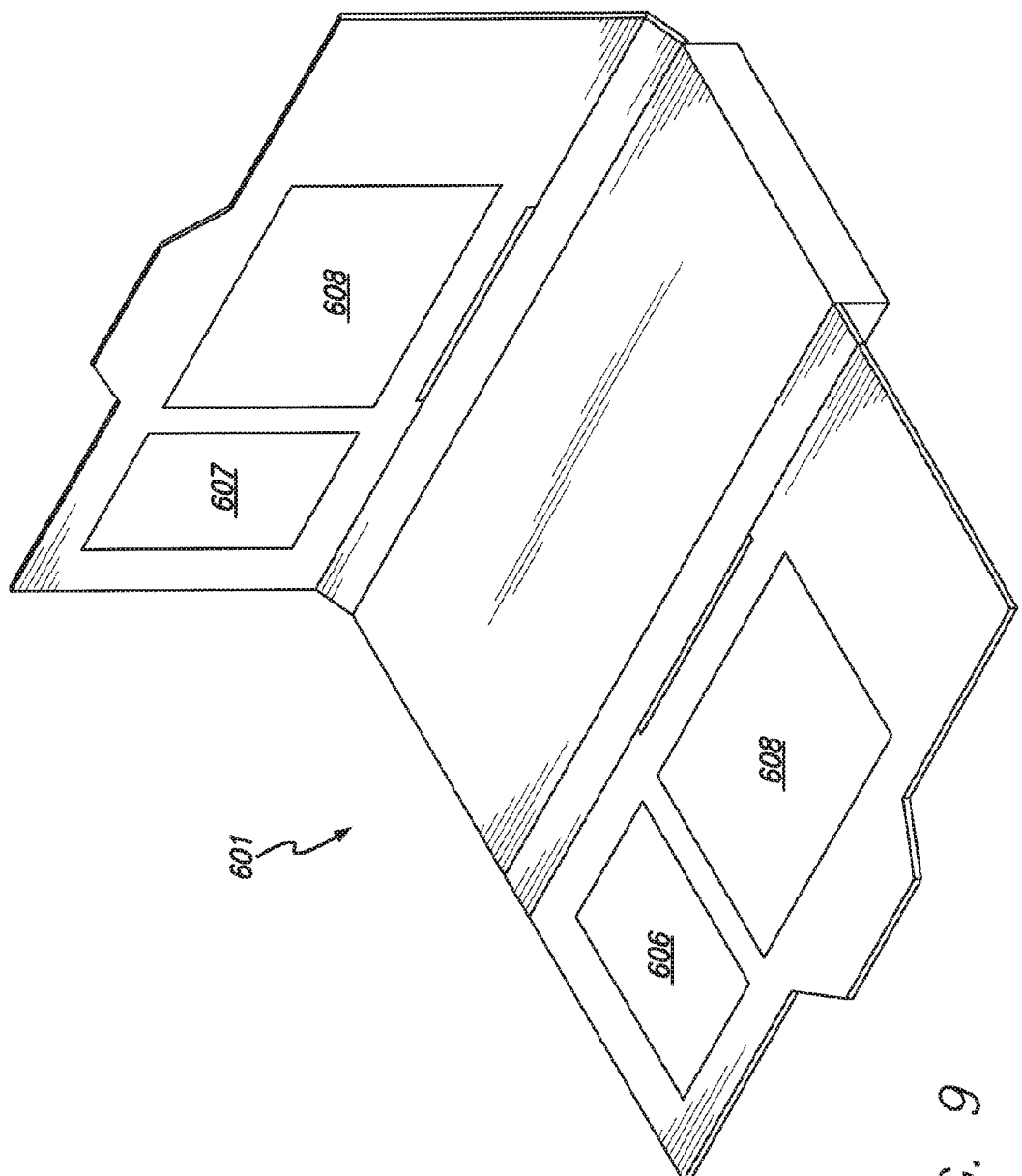
FIG. 9 is a schematic representation of the exterior surface of a carton blank showing one arrangement of the labeling information.

In addition to performing its protective functions, this carton provides surfaces upon which mandatory and desirable information can be presented. Mandatory information that must appear on the exterior surface of the carton includes identification of the kit, manufacturer, shipper and intended recipient; any pertinent product information, warnings and/or cautions (603); and any markings required by the transportation company or service (604, 605). The lot number, expiration date, and/or universal device identification code pertaining to the kit may also be required in human and/or machine readable form. Instructions for opening the carton; trade dress; patent and trademark notices; and similar information desirably may also appear on this surface. The interior surface (not shown) of this carton desirably bears the instructions for the use of the kit in at least pictorial form and may include other pertinent information. The portions (602) of the illustrative graphical layout shown in FIGS. 1, 7 and 9 are also available for bearing instructional and similar information.

The cost of applying the requisite information to the carton can be a significant contributor to the overall cost per result. The traditional approach in which much of the information that appears on the exterior of the carton is applied in the form of preprinted adhesive labels is the most flexible method, but it also tends to be the most expensive and most prone to error. Significant reductions in both cost and error rate are possible if the "static" information is preprinted on the carton by the manufacturer. Much of this static information changes rarely, if at all, over the life of the product, but it can include certain variable items such as lot codes, expiration dates and, in the case of the present kit for the self collection of samples, a replica of the unique identification code that appears on the receptacle contained within a kit. This type of information can, however, readily be accommodated by modern industrial printers. At the opposite extreme, the subject name (possibly including an identification code) and address are different for each kit and are generally not known until shortly before the kit is dispensed to the subject. Depending upon the specific circumstances, this information is usually manually written on the carton or applied as a print-on-demand adhesive label.

Cost effectively applying the name and address of the laboratory can be the most challenging aspect of this labeling. Although this labeling has traditionally been applied by the subject, the potential for errors associated with this approach makes it desirable to apply this labeling to the carton before it is dispensed to the subject. Despite the high labor and materials costs, dispensing sites that send samples of a given type to any of several laboratories generally prefer to use preprinted adhesive labels for this purpose due to the flexibility that they provide. Most dispensing sites, however, send all samples for a given type of test to a single laboratory. Alternatively, it is not unusual for sample collection kits to be dispensed by a laboratory. In these cases it is generally more cost effective for the laboratory information to be applied by the manufacturer or applied as a secondary operation by a value added distributor before the kits are provided to the dispensing site. In order to be commercially viable, the carton must be physically and economically suitable for use in any of these scenarios without modification. The carton illustrated in FIG. 1 satisfies this requirement.

To facilitate subject compliance it is desirable that the kit provided to the subject include prepaid shipping to the laboratory. This is most readily and cost effectively accomplished by preprinting or applying an appropriate pre-paid postal permit or delivery service account number (605) on the carton.

The specific embodiment that is illustrated in FIG. 1 comprises two top "flaps" that, when the package is in its folded state, lie one on top of the other. These flaps will be referred to as "subject flap" (606) and "lab flap" (607) for clarity in the following description. When the package is folded for shipment to the subject, the subject flap, which bears the shipping address of the subject (608), lies on top of the lab flap which bears the shipping address of the laboratory (609). The shipping address of the subject is therefore exposed. Both flaps desirably bear the appropriate postal or delivery account information. In the preferred version of this embodiment the subject opens both flaps to obtain access to the kit components; collects the sample in accordance with the instructions printed on the inside of the carton and the package insert; returns the support containing the receptacle and sample to the carton; and closes the two flaps such that the lab flap lies on top of the subject flap such that the laboratory address is exposed. In another variant of this embodiment the subject flap is provided with a tear strip, perforations or similar means that cause the subject to detach the subject flap from the package as it is being opened. In this instance, after inserting the support containing the collected sample into the package, the subject closes the remaining lab flap thereby exposing the address of the laboratory. The package is then delivered to the appropriate postal, delivery or shipping service.

The carton illustrated in FIG. 7 additionally comprises three compartments. In this instance the center compartment is intended to hold the support with any of its content; the collection device during shipment to the subject; and, if necessary, a second collection device and/or a package insert while the two outer compartments (610) are intended to hold as needed any ancillary materials such as, but not limited to a container of preservative solution if the preservative is shipped in a package other than the receptacle and a disposable glove or forceps that may be included for sanitary reasons and/or to minimize the potential for contamination of the collection device while it is being handled by the subject. The number and dimensions of these compartments can be adapted as appropriate to any particular use of the kit.

EXAMPLE 9

Sample Recovery

The present invention is intended to facilitate the processing of received samples by the laboratory and to reduce the potential for the misidentification of samples.

The unique identification code (404) that is applied to each receptacle as described in Example 4 and is preferably also reproduced on the external packaging as described in Example 8 is a significant element in the "Positive ID" systems used by many laboratories to ensure that the correct result is returned for each subject. These codes are preferably presented in both human and machine readable formats to maximize compatibility with the various Positive ID systems that are in use.

The mechanics of recovering a LBP sample from the container used to ship it to the laboratory are often complicated by the presence of the sample collection device in the container. In such cases a laboratory technician typically either attempts to pour the sample into another container while leaving the collection device in the original container or attempts to remove the collection device from the original container using forceps or similar means. In addition, if the sample was collected using an adsorbent device, it is often necessary to recover the portion of the sample that was adsorbed by the device, typically by squeezing or pressing the device and collecting any fluid that is expressed. These labor intensive procedures increase both the cost of sample processing and the potential for sample loss or contamination.

The present disclosure addresses these limitations. The end of the receptacle opposite to the press seal is provided with a sealed tip (403) that is shaped to permit simple and efficient transfer of the sample from the receptacle into a container such as a centrifuge tube in preparation for processing. In use, the technician opens the tip by cutting or by tearing along the perforations optionally provided and decanting the liquid into the desired container. As the tip is smaller than the collection device, the device remains in the receptacle. Sample adsorbed by the collection device can be recovered by squeezing or pressing the collection device while it remains in the receptacle and collecting the expressed fluid in the same container that holds the remainder of the sample. This squeezing or pressing can be done manually or by use of roller tongs or similar devices known in the art.

The invention claimed is:

1. A packaging for a biological material comprising:
   a flexible receptacle comprising a primary reclosable sealing means, the flexible receptacle containing a preservative and the biological material suspended or dissolved in the preservative, the preservative in direct contact with an inside surface of the flexible receptacle, the primary reclosable sealing means preventing flow of the preservative from the flexible receptacle when in a closed position;
   a rigid reclosable support containing the flexible receptacle, wherein said support comprises one or more additional sealing means for said receptacle; and
   wherein the one or more additional sealing means creates one or more pinch points in the flexible receptacle adjacent the primary reclosable sealing means, the one or more additional sealing means preventing flow of the preservative from the flexible receptacle.

2. The flexible receptacle of claim 1 wherein said primary reclosable sealing means comprises one of a press seal, a zipper seal, a screw seal, and a snap seal.

3. The packaging of claim 1, wherein the one or more pinch points are configured to prevent failure of the primary reclosable sealing means of said flexible receptacle.

4. The packaging of claim 1, wherein said preservative is in liquid or solid form, and wherein said one or more pinch points is located between a substantial portion of said preservative and said primary reclosable sealing means.

5. The packaging of claim 4, wherein failure of the primary reclosable sealing means of said flexible receptacle is prevented by limiting forces from said preservative applied to said primary reclosable sealing means by blocking a portion of said preservative from interacting with said recloseable sealing means at said one or more pinch points.

6. The packaging of claim 1 further comprising a second reclosable support, said second reclosable support enclosing said reclosable support.

7. The packaging of claim 6, wherein said second reclosable support further comprises provision for enclosing at least one of additional materials and supplies that are at least one of necessary and useful in the collection of said biological material.

8. A method of packaging a biological material, the method comprising:
   collecting the biological material on a collection device;
   inserting a preservative into a flexible receptacle, the flexible receptacle including a primary reclosable sealing means;
   placing the collecting device in the flexible receptacle such that the biological material is suspended or dissolved in the preservative, and wherein an inside surface of the flexible receptacle is in direct contact with the preservative;
   closing the primary reclosable sealing means such that the primary reclosable sealing means prevents flow of the preservative from the flexible receptacle;
   placing the flexible receptacle in a rigid reclosable support, the rigid reclosable support including one or more additional sealing means;
   closing the rigid reclosable support such that the primary reclosable sealing means of the flexible receptacle is located outside the rigid reclosable support; and
   creating a pinch point in the flexible receptacle through the one or more additional sealing means of the rigid reclosable support, the one or more additional sealing means preventing flow of the preservative from the flexible receptacle.

9. The method of claims 8, the method including the step of inserting the preservative as a liquid or solid into the flexible receptacle before closing the primary reclosable sealing means.

10. The method of claim 8, wherein the pinch point in the flexible receptacle is adjacent the primary reclosable sealing means.

11. A packaging for a clinical sample comprising a suspension or solution of a biological material in a fluid, the packaging comprising:
- a flexible receptacle comprising a primary reclosable sealing means, wherein the fluid of the clinical sample is in direct contact with an inside surface of the flexible receptacle, and wherein the primary reclosable sealing means prevents flow of the fluid from the flexible receptacle when in a closed position;
- a rigid reclosable support containing the flexible receptacle, wherein said support comprises one or more additional sealing means for said receptacle; and
- wherein the one or more additional sealing means creates one or more pinch points in the flexible receptacle adjacent the primary reclosable sealing means, the one or more additional sealing means preventing flow of the fluid from the flexible receptacle.

* * * * *